(12) United States Patent (10) Patent No.: US 6,496,722 B1
Schmidt (45) Date of Patent: Dec. 17, 2002

(54) EVALUATION OF ELECTROCARDIOGRAMS IN THE FIELD OF EXTRASYSTOLES

(76) Inventor: Georg Schmidt, Belgradstrasse 19, D-80796 Muenchen (DE)

( * ) Notice: Subject to any disclaimer, the term of this patent is extended or adjusted under 35 U.S.C. 154(b) by 0 days.

(21) Appl. No.: 09/554,033

(22) PCT Filed: Nov. 5, 1998

(86) PCT No.: PCT/DE98/03225

§ 371 (c)(1),
(2), (4) Date: Jun. 23, 2000

(87) PCT Pub. No.: WO99/23944

PCT Pub. Date: May 20, 1999

(30) Foreign Application Priority Data

Nov. 7, 1997 (DE) .......................... 197 49 393

(51) Int. Cl.[7] ........................................... A61B 5/0402
(52) U.S. Cl. ........................................... 600/513
(58) Field of Search ........................ 600/513, 515, 600/516, 521

(56) References Cited

U.S. PATENT DOCUMENTS

| 3,658,055 A | * | 4/1972 | Abe et al. ........... 600/515 |
| 3,881,467 A | * | 5/1975 | Stanly et al. ........ 600/515 |
| 4,499,904 A | * | 2/1985 | Sidorenko et al. ... 600/516 |
| 5,313,954 A | * | 5/1994 | Schwarze et al. .... 600/515 |

FOREIGN PATENT DOCUMENTS

GB    2190505   * 11/1987   ............ A61B/5/02

* cited by examiner

Primary Examiner—Jeffrey R. Jastrzab
(74) Attorney, Agent, or Firm—Milde & Hoffberg, LLP

(57) ABSTRACT

The time intervals between successive heartbeats (6,6) directly before and after an extrasystole (7) are determined in order to evaluate electrocardiograms, whereby both sequences are compared with each other. The time intervals from the sequence before the extrasystole are used to form a reference value.

24 Claims, 5 Drawing Sheets

EVALUATION OF ELECTROCARDIOGRAMS IN THE FIELD OF EXTRASYSTOLES

BACKGROUND OF THE INVENTION

The invention relates to a method and a device for evaluating electrocardiograms (EKG) in the area of extrasystoles.

Extrasystoles are heartbeats that occur prematurely outside the regular base rhythm; they may occur individually, in twos as so-called couplets or in groups as salvos. According to the location of their origin, the extrasystoles are basically divided into vestibular or supra-ventricular extrasystoles and ventricular extrasystoles. Even today, cause and origin of extrasystoles are still not entirely understood. There is a complex interaction of local factors (in the heart muscle) and overriding structures (in the autonomous nervous system).

Extrasystoles are classified by their type, the frequency of their occurrence, their form and their location of origin. The detection of frequent and repetitive extrasystoles has gained a certain importance in estimating the prognosis of persons who had just undergone a heart attack. However, the detection of extrasystoles in long-term EKGs is not very specific; extrasystoles do not only occur in ill persons but also in healthy ones. It is therefore difficult, if not impossible to derive at therapeutic consequences, for example the prophylactic implantation of a cardio-vortex defibrillator, from an extrasystole for individual patients. Other available methods of risk stratification are relatively unreliable as well. It would be great progress if the individual risk could be determined more accurately than before using parameters that are coupled with extrasystoles.

SUMMARY OF THE INVENTION

It is therefore, the principal objective of the invention to specify a method and a device for evaluating electrocardiograms in the area of extrasystoles in order to provide parameters that can be related to the individual risk of a person.

This objective is accomplished according to the invention for a method and a device of the referenced type which caries out the following steps:

(a) after recognizing an extrasystole, determining characteristic attributes of at least the heartbeats occurring in a continuous sequence following the extrasystole, and (b) quantifying these attributes using an analysis method.

It has been found that extrasystoles leave characteristic signatures in the base rhythm that can be used for risk stratification. For persons with a normal or slightly increased risk, as a rule, the heart beat sequence following an extrasystole usually accelerates, but only for a few heartbeats (transient frequency increase), which is then followed by a phase of frequency decrease of the heartbeat sequence. The heart frequency then levels off to its initial level after about ten to twenty heart actions (transient frequency decrease, see FIG. 3). For persons with an increased risk, this characteristic reaction is significantly weaker or missing altogether. In these cases, often a more or less erratic heartbeat sequence, that is, one without order, can be found.

Basically, various options are available to quantify these differences, for example using analysis methods in the time or frequency domains.

Using the time domain, the following parameters have proven useful in estimating the risk:

"Onset": Difference of the mean values of the last normal RR intervals preceding the extrasystole and the first normal RR intervals following the extrasystole; preferably, two RR intervals each immediately preceding and following the extrasystole are used.

"Slope": Greatest frequency decrease within a sequence of several, e.g., 20 heart beat intervals determined following an extrasystole across, preferably, five successive RR intervals as slope of the regression line.

"Correlation coefficient of the slope": A measure for the regularity of the slope and generated by numeric mean value generation of several successive slope values.

All quantities mentioned have proven suitable for risk stratification: With a small onset, a flat slope or a low correlation coefficient of the slope, the risk of dying in the continued course is significantly increased. With a considerable onset, steep slope or high correlation coefficient of the slope, the risk is normal or significantly lower.

In the frequency domain, the low- or high-frequency portions can be quantified and their ratio can be determined: When the high-frequency portions increase, the risk of dying in the continued course is higher. If the low-frequency portions increase, the risk is normal or significantly lower.

In a multi-variant analysis, the new risk parameters proved to be largely independent of all other risk parameters used thus far. This means, that a significant portion of the information contained in them is indeed new, that is, clinically additive.

When investigating the vestibular extrasystoles, such associations of the slope and the correlation coefficient of the slope with the mortality risk were found as well.

A device for evaluating electrocardiograms in the area of extrasystoles can also be integrated directly in an instrument for recording the electrocardiograms, particularly long-term electrocardiograms. This instrument then not only provides the actual EKG, but also the evaluation with regard to the time behavior of the heartbeats preceding and following an extrasystole. The integration of such a device according to the invention into a pacemaker or into an implanted defibrillator is conceivable as well.

In general, extrasystoles are easily recognized in an EKG, because the time behavior and—in the case of the ventricular extrasystoles—its shape changes visibly compared to the regular base rhythm. Thus, a sequence preceding an extrasystole can be clearly differentiated from a sequence following an extrasystole.

It is, otherwise, also possible to use the method according to the invention for clinical research regarding the effect of medication. It has been found that with the help of onset, slope and correlation coefficient of the slope, patients with varying effects of an antiarrhythmic medication can be identified. The more pronounced the onset, slope and correlation coefficient are in the treatment of patients, the more effective the medication will be classified.

For a full understanding of the present invention, reference should now be made to the following detailed description of the preferred embodiments of the invention as illustrated in the accompanying drawings.

DESCRIPTION OF THE PREFERRED EMBODIMENT

Figure 1:
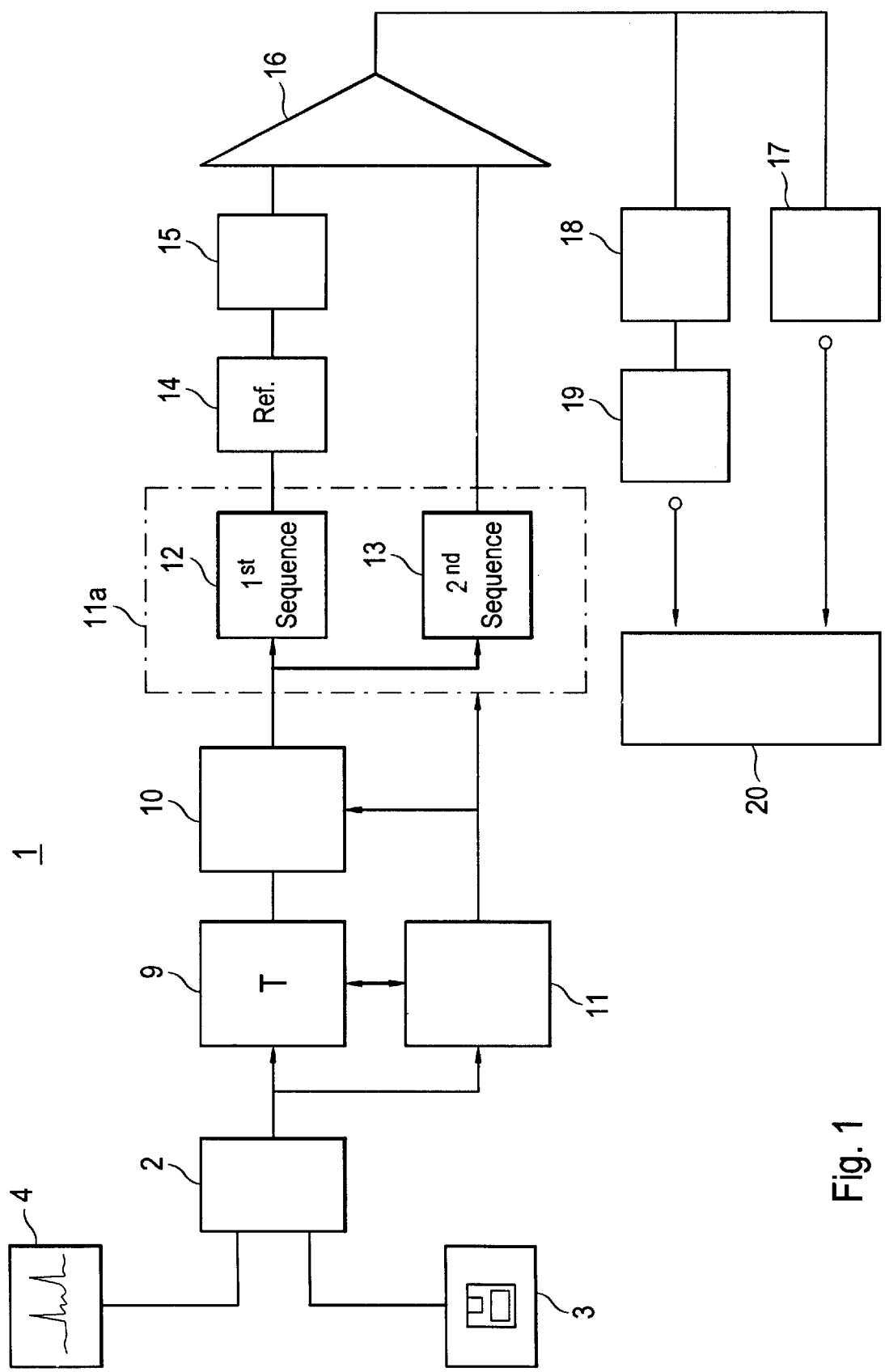
FIG. 1 shows a device for evaluating electrocardiograms in the area of extrasystoles according to the invention - - -.

The preferred embodiments of the present invention will now be described with reference to FIGS. 1–7 of the drawings. Identical elements in the various figures are designated with the same reference numerals.

FIG. 1 shows a device 1 for evaluating electrocardiograms. This device has an input unit 2 that is supplied with data from a long-term electrocardiogram. This is carried out either via a data carrier 3 where one or several long-term electrocardiograms are recorded, or via an electrocardiograph 4 that is used to record a long-term electrocardiogram of a person.

Figure 2:
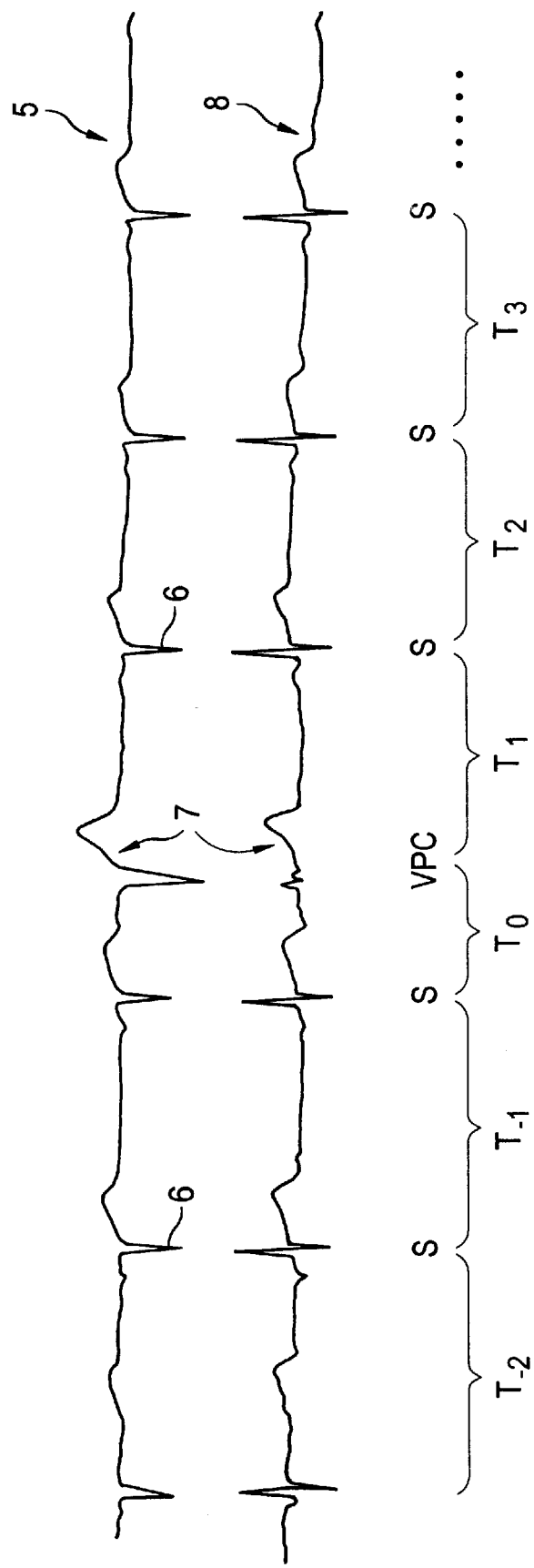
FIG. 2 shows a section of 24-hour electrocardiogram of a post infarct patient in the area of the ventricular extrasystole - - -.

The top line of FIG. 2 shows a section of an EKG 5, where the base rhythm is recognizable by the R-spikes 6. A ventricular extrasystole (VES) 7 that disturbs the regular base rhythm of the heartbeats is visible between the second and third spike. The second line of FIG. 2 shows the time derivative of the EKG 5, where the prominent interruption of the regular base rhythm through the extrasystole 7 is recognizable as well.

The third line of FIG. 2 shows the time intervals between the individual heartbeats, namely the time intervals T-2 and T-1 immediately preceding the extrasystole, then the shortened time interval Tk between the last heartbeat preceding the extrasystole and the extrasystole and then following the time intervals Tp between extrasystole and first regular heartbeat as well as, following, between two back to regular heartbeats each T1, T2, T3, . . .

In the device 1, an interval measurement circuit 9 determines these intervals Ti; the interval sequence is supplied to a first memory 10. In a discriminator circuit 11, that is also supplied with the data of the EKG and that is connected with the measurement circuit 9, the extrasystole is recognized and marked based on the time specification of the EKG and the time derivation according to the plot 8. This result is supplied to the first memory 10 and a separator circuit 11, where the sequence of heartbeats is separated into a first sequence immediately preceding the extrasystole and a second sequence immediately following the extrasystole. These two sequences are each stored in a memory 12 and 13, respectively. A mean value of these time intervals is generated in a mean value generator 14 from a specified number of time intervals of the first sequence, in this case, the time intervals T-2 and T-1 immediately preceding the extrasystole and is stored as reference value R in a memory 15.

Figure 3:
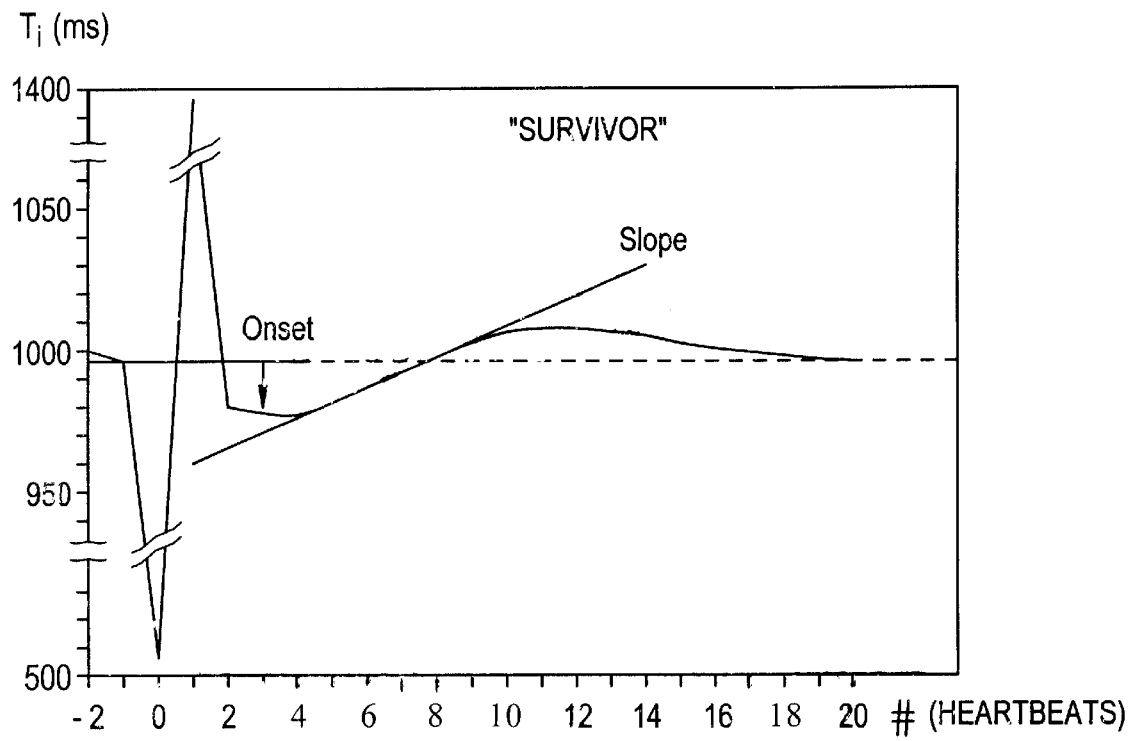
FIG. 3 is a diagram that displays the time intervals between two successive heartbeats in the area around an extrasystole for a patient with low mortality risk - - -.
Figure 4:
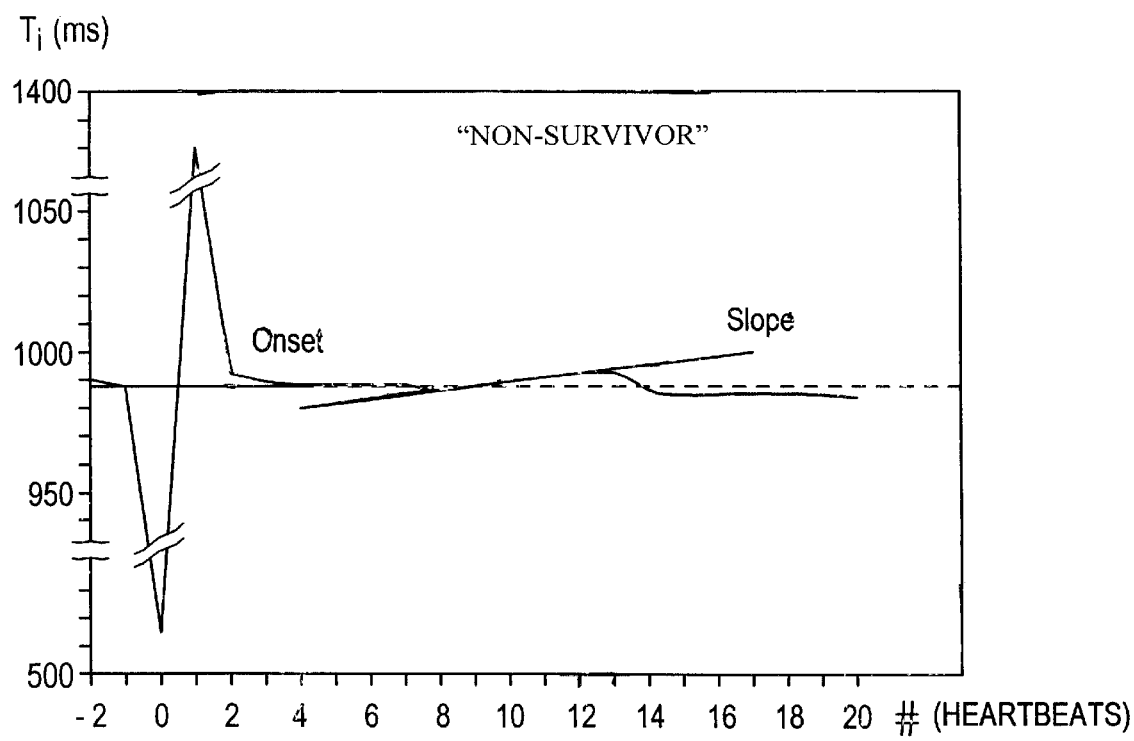
FIG. 4 is a diagram that displays the time intervals between two successive heartbeats in the area around an extrasystole for a patient with high mortality risk - - -.

In a comparison circuit 16, the time intervals immediately following the extrasystole, that is, the time intervals T1, T2, T3, etc. are compared to a mean value stored in the memory 15. The deviation or difference between both values and the number of the respective time intervals from the sequence and the extrasystole are provided at the output of the comparison circuit and supplied to a first output unit 17 and may be displayed there. A schematic display is shown in FIGS. 3 and 4: The time in milliseconds for the respective measured time intervals is entered on the y-axis of each diagram; the numbers, that is, the indices of the individual time intervals are entered at equally spaced points on the x-axis. In FIG. 3, one can see that after the significant time deviations of the extrasystole 7, the time intervals T2, T3, T4 and so on are initially shortened between again almost regular occurring R-spikes. Thereafter, beginning around time interval T5, a counter-reaction occurs with time intervals getting longer than the reference value starting at time interval T7. Thereafter, the time behavior swings back towards the reference value, which is reached at about time interval T18. The individual measurement points can be connected with an almost smooth curve plot.

The diagram shown in FIG. 4 is from a different patient: It becomes clear that the time intervals following the extrasystole 7, practically do not depart from the mean value; only insignificant, almost statistical deviations are present.

The data obtained in the comparison circuit 16 is supplied to a plot evaluation circuit 18 or also to an output circuit 17.

In this evaluation circuit 18, the plot generated in FIGS. 3 and 4 by connecting all measurement points, is evaluated with regard to its slope in relation to the x-axis. This is done according to a simple algorithm with a few specifications, e.g., in this case the evaluation of five successive measurement points each. In this plot evaluation 18, the section of the plot that exhibits the greatest slope in relation to the x-axis is marked. This is shown in FIGS. 3 and 4 as well. One can see that between time intervals T5 and T9 the plot shown in FIG. 3 exhibits a significant slope in relation to the x-axis, while such a slope is practically non-existent in the plot of FIG. 4.

The described plot evaluation can be carried out based on a single plot following an extrasystole; however, more significant statements can be made if several plots (in the case of several extrasystoles) can be superimposed and averaged after a certain normalization regarding the reference value. The trend whether a significant slope is present or not becomes much clearer by such a superimposition. The result of the plot evaluation 18 is supplied to a second output unit 19 and can be output in a conventional manner, for example, displayed or printed. The results available in the output units 17 and 19 can also be stored in a data carrier 20, for example.

Figure 5:
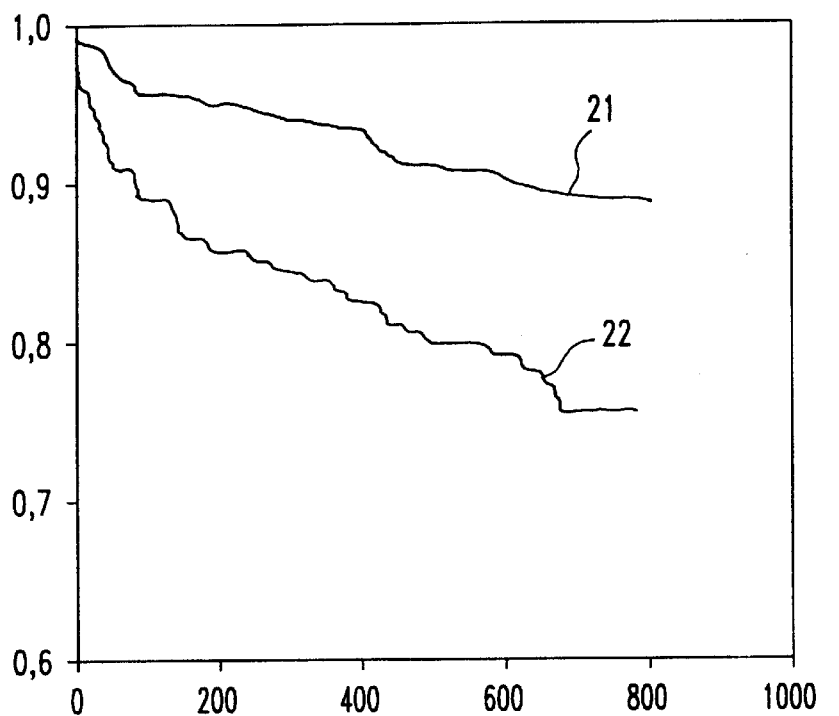
FIG. 5 is a diagram of the survival probability of patients with pronounced and weakened or non-existent onset - - -.
Figure 6:
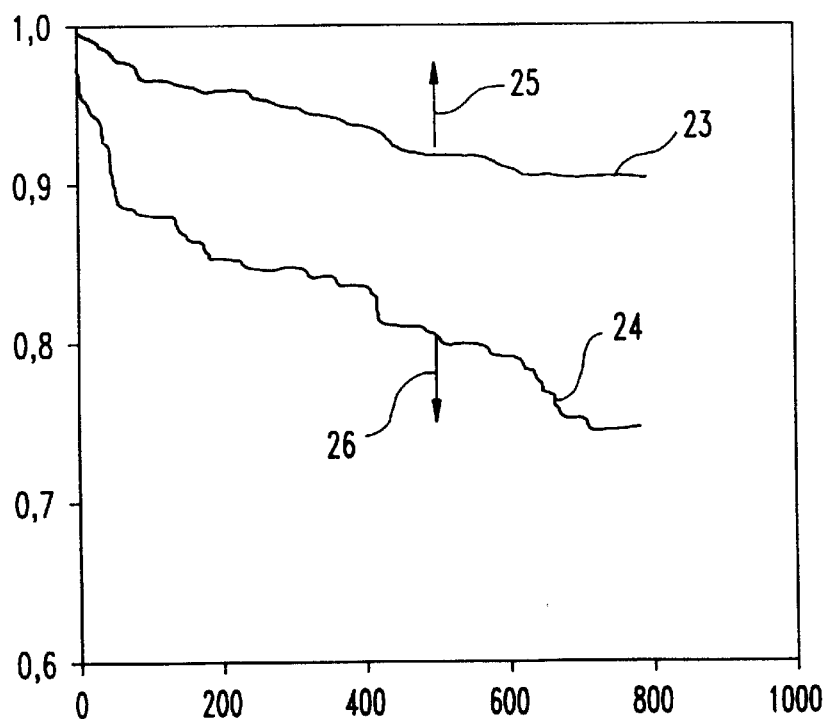
FIG. 6 is a diagram of the survival probability of patients with pronounced and weakened or non-existent slope - - -.
Figure 7:
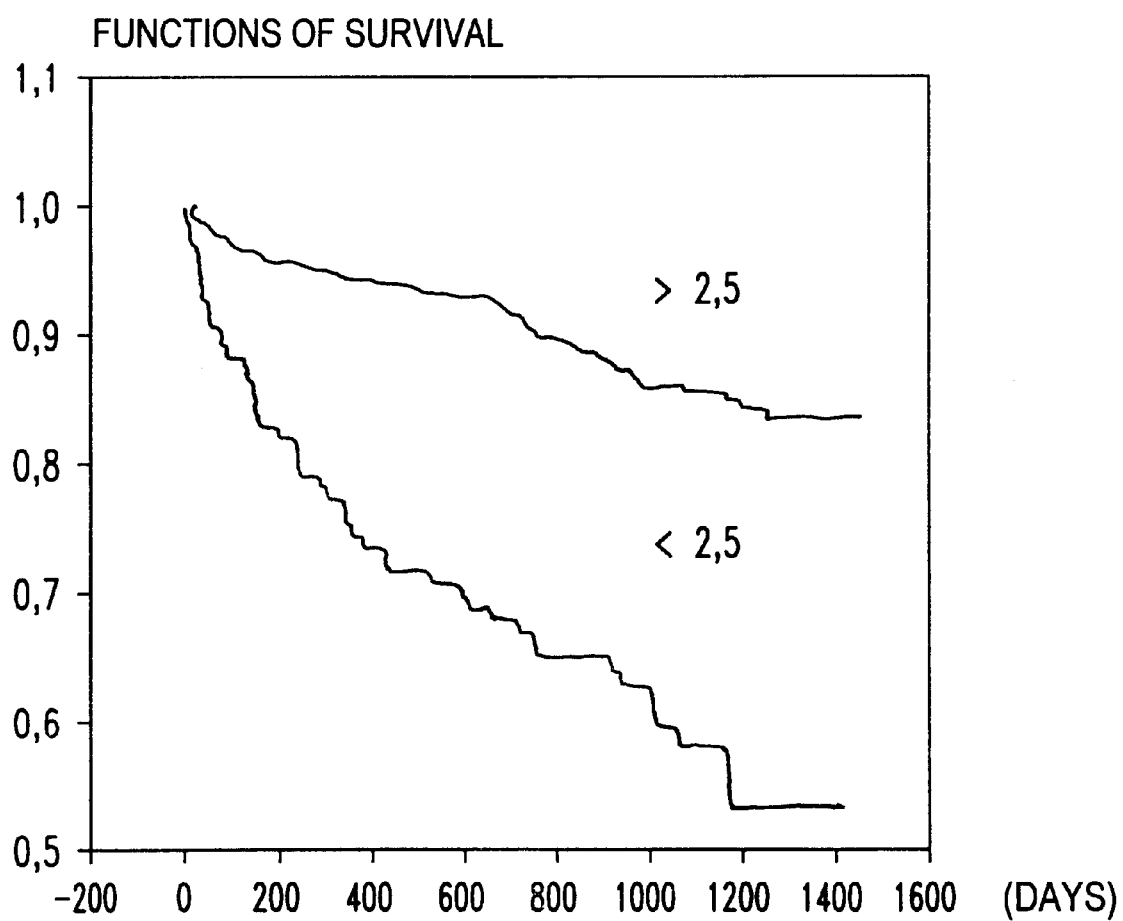
FIG. 7 is a diagram of the survival probability of patients with a high and a low correlation coefficient of the slope.

In FIGS. 5 and 6, the survival function of post infarct patients is plotted over the time in days based on the data of several thousand EKG long-term examinations of such patients. In FIG. 5, the plot 21 is related to those patients where the time behavior of the heartbeats immediately following an extrasystole with regard to the onset deviated significantly from the reference value, while plot 22 presents the survival function of patients, where no significant deviation occurred, that is, that results were present according to FIGS. 3 and 4. One notices that about 95% of the patients, where a significant deviation was present, were still alive after one year, while this was only true for 85% of the patients, where no significant deviation was measured.

FIG. 6 shows two similar plots 23 and 24, where the survival function is plotted under consideration of the slope described above. Here too one can observe that after about a year about 95% of patients with a significant slope were still alive, while this percentage dropped to 85% as well for patients with no or an insignificant slope. The curves of FIGS. 5 and 6 show comparable results; obviously both parameters offer good statements in the case of ventricular extrasystoles.

This means, when evaluating electrocardiograms of a person, a relatively low mortality risk can be assumed for a pronounced onset and slope following an extrasystole, while a relatively high mortality risk can be assumed for a small or for no deviation in the onset and an insignificant slope. Based on this evaluation, possibly in connection with other examinations, a physician can make a diagnosis and initiate a suitable therapy of the examined person.

The presented evaluation method for onset and slope can be employed directly for clinical tests of medication. For this purpose, groups of persons are divided into two groups each that show significant changes in onset and slope or that do not show such significant changes, respectively. After a long-term examination, it can be directly concluded based on the statistical data, whether by administering medication an improvement of the survival function occurred, as is indicated by the arrow 25 in FIG. 6 for patients with a relatively stable physiological condition, for example, or whether the situation worsened, as is indicated by the arrow 26 pointing downward for patients without significant changes in onset and slope.

Based on the evaluation of thousands of electrocardiograms stored on data carriers, the criterion of a significant slope appears to be a pronounced criterion for all extrasystoles, while a significant onset is an equally pronounced criterion for ventricular extrasystoles only. For vestibular extrasystoles, that is, basically for premature normal heartbeats, the onset exhibits practically no changes following the extrasystole; a change occurs only after several heartbeats resulting in a significant change of the slope.

The preceding described that after recognizing an extrasystole, the time intervals preceding and following the extrasystole are evaluated; however, other characteristic attributes of the evaluated heartbeats may be used as well, such as, for example, the frequency behavior mentioned above, or the frequency composition of the individual heartbeats. It is additionally also possible to evaluate only the heartbeats that occur following an extrasystole and to quantify them in an analysis process. The quantification does not need to be carried out based on a reference value; for example, the time deviations of the heartbeats that occur following the extrasystole beginning with the time interval of the first heartbeat following the extrasystole can be evaluated.

There has thus been shown and described a novel evaluation of electrocardiograms in the area of extrasystoles which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

I claim:

1. Method for evaluating electrocardiograms of patients in the area of recognized extrasystoles, comprising the steps of:
   (a) after recognizing an extrasystole, determining characteristic attributes of heartbeats occurring in a continuous sequence immediately preceding and following the extrasystole; and
   (b) quantifying these attributes using an analysis method to produce a result.

2. Method as set forth in claim 1, wherein the quantified result is compared to a reference value.

3. Method as set forth in claim 1, wherein the heartbeats are analyzed in their characteristics with regard to time behavior.

4. Method as set forth in claim 1, comprising the steps of:
   determining time intervals between successive heartbeats;
   after recognizing an extrasystole, determining the time intervals between successive heartbeats of a continuous sequence of heartbeats immediately preceding and following an extrasystole;
   comparing the time intervals of the sequence following the extrasystole to a reference value corresponding to a time interval of the sequence preceding the extrasystole, for each heartbeat marking respective time intervals of the sequence following the extrasystole and an associated deviation from the reference value; and
   determining a progression of the time intervals and of deviations in the sequence following the extrasystole and the apparent trends of these values in a direction toward the reference value.

5. Method as set forth in claim 4, wherein a mean value serving as a reference value is generated from at least two successive time intervals of the sequence preceding the extrasystole, and wherein the time intervals of the sequence following the extrasystole are compared to this reference value.

6. Method as set forth in claim 5, wherein two time intervals immediately preceding the extrasystole are used to generate the mean value.

7. Method as set forth in claim 4, wherein successive numbers are assigned to the successive time intervals marked for each heartbeat, wherein deviations of the marked time intervals from the reference value are plotted as a function of the number of the respective time interval, and wherein a trend plot of this section compared to this reference value line is generated by using a certain number of successive deviations.

8. Method as set forth in claim 4, further comprising the steps of superimposing comparison results for the sequences of time intervals following differing extrasystoles and averaging individual values.

9. Method as set forth in claim 8, further comprising the step of normalizing the comparison results prior to the step of superimposing.

10. Method as set forth in claim 8, further comprising the step of evaluating the time intervals following an extrasystole with regard to the heartbeats following the extrasystole and deviating in an onset from a base rhythm.

11. Method as set forth in claim 4, wherein several successive time intervals following an extrasystole are evaluated with regard to a slope progression in comparison to a line of the reference value.

12. Method as set forth in claim 11, wherein the slope progression following several successive extrasystoles are added and averaged to form a correlation coefficient.

13. Method as set forth in claim 4, wherein the sequence of time intervals immediately preceding the extrasystole that is to be evaluated is comprised of one to five time intervals and the sequence immediately following the extrasystole is comprised of up to fifty time intervals.

14. Method as set forth in claim 13, wherein the sequence of time intervals immediately preceding the extrasystole that is to be evaluated is comprised of two time intervals and the sequence immediately following the extrasystole is comprised of up to fifty time intervals.

15. Method as set forth in claim 13, wherein the sequence immediately following the extrasystole that is to be evaluated is comprised of one to five time intervals and the sequence immediately following the extrasystole is comprised of between ten and twenty time intervals.

16. Device for evaluating electrocardiograms in the area of extrasystoles for carrying out the method set forth in claim 15, comprising means for registering characteristic attributes of the heartbeats of continuous sequences immediately preceding and following the extrasystole and for quantifying these attributes.

17. Device as set forth in claim 16, comprising, in combination:
- a first device for determining the time intervals (Ti) between two successive heartbeats of a continuous sequence of heartbeats;
- a first memory for storing the time intervals of said sequence;
- a second device for marking an extrasystole;
- a third device for splitting the stored time intervals at the occurrence of an extrasystole into one sequence immediately preceding and one sequence immediately following the extrasystole;
- a fourth device for generating a reference value from at least one time interval of the sequence preceding the extrasystole;
- a second memory for storing said reference value;
- a fifth device for comparing the time intervals of the sequence immediately following the extrasystole to the stored reference value; and
- a sixth device for producing the output of the comparison results.

18. Device as set forth in claim 11, wherein the third device exhibits two memories for storing the first and the second sequence of time intervals, respectively.

19. Device as set forth in claim 17, wherein the fourth device generates a mean value from at least two successive time intervals immediately preceding the extrasystole to serve as a reference value.

20. Device as set forth in claim 11, wherein the output of the fifth device is connected to a plot evaluation circuit for calculating the trend progression of a sequence of a specified number of successive time intervals following an extrasystole compared to the reference value.

21. Use of the method set forth in claim 1 for examining the effectiveness of antiarrhythmic medication by examining in long-term examinations the time behavior of successive heartbeats preceding and following extrasystoles for several groups of patients and generating diagrams for the likelihood of survival as a result.

22. Method as set forth in claim 1, wherein the heartbeats are analyzed and quantified in their characteristic with regard to frequency behavior.

23. Method as set forth in claim 22, wherein low and high frequency portions of the individual heartbeats are quantified and compared. to respective reference values.

24. Use of the method set forth in claim 1, for examining the effectiveness of antiarrhythmic medication by examining, in long-term examinations, time behavior and frequency behavior of successive heartbeats preceding and following extrasystoles for several groups of patients and generating diagrams for the likelihood of survival as a result.

* * * * *